United States Patent [19]

Huth et al.

[11] Patent Number: 4,460,573

[45] Date of Patent: Jul. 17, 1984

[54] METHODS OF STABILIZING THIMEROSAL IN PRESENCE OF POLYVINYLPYRROLIDONE

[75] Inventors: Stanley W. Huth, Newport Beach; Hali G. Wagner, Norco, both of Calif.

[73] Assignee: Allergan Pharmaceuticals, Inc., Irvine, Calif.

[21] Appl. No.: 506,579

[22] Filed: Jun. 22, 1983

[51] Int. Cl.$^3$ .................. A61K 31/79; A61K 31/305; A01N 55/06
[52] U.S. Cl. .................................... 424/80; 424/291
[58] Field of Search ................................ 424/80, 291

[56] References Cited

U.S. PATENT DOCUMENTS 3,755,561 8/1973 Rankin .................................. 424/80
3,888,782 6/1975 Boghosian et al. ................... 424/80
4,029,817 6/1977 Blanco et al. ......................... 424/80
4,120,949 10/1978 Bapatla et al. ....................... 424/80

Primary Examiner—Douglas W. Robinson
Attorney, Agent, or Firm—Joseph A. Marlino; Stuart R. Suter; Alan D. Lourie

[57] ABSTRACT

A method of preparing solutions containing thimerosal and polyvinylpyrrolidone which results in improved stability of thimerosal is disclosed. The method involves applying a certain amount of heat to the polyvinylpyrrolidone while it is in aqueous solution and prior to its combination with thimerosal. The required thermal input to the polyvinylpyrrolidone solution is a function of four variables: solution temperature, heating time, external pressure and polyvinylpyrrolidone concentration. Advantageously this method may be employed in the manufacture of contact lens solutions.

6 Claims, No Drawings

METHODS OF STABILIZING THIMEROSAL IN PRESENCE OF POLYVINYLPYRROLIDONE

This invention relates to a method of preparing stable thimerosal solutions particularly suitable for contact lens care and ophthalmic preparations. These solutions may also be suitable for other therapeutic indications.

Thimerosal is employed as an antibacterial-antifungal agent. Numerous commercial contact lens care solutions contain the combination of thimerosal as a preservative and polyvinylpyrrolidone (Povidone, PVP) as a soothing agent. It is known that under normal conditions of manufacture thimerosal is degraded in the presence of PVP. The amount of thimerosal degradation is related to the concentration of PVP present.

An analysis of several of the above noted PVP-thimerosal containing commercial contact lens care solutions showed that as little as 25% of the label claim of thimerosal was present. For example, the following table demonstrates the loss of thimerosal experienced by commercial products which also contain PVP. These products were assayed for thimerosal prior to their expiration dating.

TABLE I

| PRODUCT INFORMATION AND HPLC ASSAY RESULTS | | |
| --- | --- | --- |
| Commercial Product | Label Claim | Approximate Thimerosal Concentration (ppm) |
| A | Povidone 10 ppm Thimerosal | 8 |
| B | Povidone 10 ppm Thimerosal | 9 |
| C | Povidone (1.67%) 40 ppm Thimerosal | 10 |
| D | Povidone 40 ppm Thimerosal | 24 |
| E | Povidone 40 ppm Thimerosal | 23 |
| F | Povidone 40 ppm Thimerosal | 25 |

It is therefore an object of this invention to provide a process of manufacturing solutions containing PVP and thimerosal which results in stabilization of the thimerosal compound.

Briefly, the invention provides a process for preparing a stable thimerosal-PVP solution by heating the PVP solution prior to its combination with thimerosal. A safe thermal input is applied to the PVP solution without changing the PVP polymer itself. The required thermal input to the PVP solution is a function of four variables: solution temperature, heating time, external pressure and PVP concentration having the following ranges:

| Variable | Range |
| --- | --- |
| Solution temperature | 85–121° C. |
| Heating time | 30–180 minutes |
| External pressure | Atmospheric-Atmospheric + 15 PSI |
| PVP Concentration in complete formula | 0.01–1.0% W/V |

The following table illustrates the criticality and interrelationship of the selected ranges.

TABLE II

| Lot No. | Final Conc. of PVP | Conc. of Thimerosal | Solution Temperature | Heating Time | Vessel Pressure |
| --- | --- | --- | --- | --- | --- |
| 026 | 0.3 | 23.0 ppm | 25° C. | 0 | Atmos*# |
| 5528 | 0.3 | 23.0 ppm | 121° C. | 90 min | Atmos + 15 PSI* |
| 5453 | 0.3 | 23.0 ppm | 85° C. | 80 min | Atmos* |
| — | 0.01–1.0 | 23.0 ppm | 85° C. | 15 min | Atmos*# |
| — | 0.3 | 23.0 ppm | 121° C. | 30 min | Atmos + 15 PSI* |
| — | 0.3 | 23.0 ppm | 121° C. | 90 min | Atmos + 15 PSI* |
| — | 1.0 | 23.0 ppm | 121° C. | 90 min | Atmos + 15 PSI* |
| — | 4.0 | 23.0 ppm | 121° C. | 90 min | Atmos + 15 PSI*# |
| 5591 | 0.3 | 23.0 ppm | 121° C. | 60 min | Atmos + 15 PSI* |
| 5421 | 0 | 23.0 ppm | 25° C. | 0 | Atmos* |

*Atmospheric
Combination of variables resulted in thimerosal degradation

Table II also illustrates how the variables are interrelated. For example, at a higher temperature and pressure, less heating time is required, compare lots 5453 and 5591 which are both stable.

In a preferred embodiment, the PVP solution is autoclaved at 121° C. at atmospheric plus 15 PSI pressure for about 90 minutes.

In regard to the stability of the solutions listed in Table II, Lot 5421 which did not contain any PVP showed perfect stability, i.e., there was no loss of thimerosal after being stored at room temperature for 85 days.

Lot 026 which had no thermal input, i.e., manufactured under normal conditions, resulted in a dramatic loss of thimerosal. When stored at room temperature for 50 days, the thimerosal concentration was reduced from 23.0 ppm to 12.90 ppm.

In contrast to this, lot 5528 which also contained 23.0 ppm of thimerosal and was prepared according to the process of this invention assayed 23.0 ppm at the end of 71 days. In brief, when following the process of this invention which comprises separately heating a PVP solution before the addition of thimerosal, a stable thimerosal solution results.

The solutions of this invention can contain in addition to the PVP and thimerosal a pharmaceutical carrier, preferably a sterile ophthalmic vehicle. Exemplary of liquid ophthalmic carriers include standard 1.9% isotonic boric acid, 0.9% sodium chloride or sodium borate solutions. Conventional buffering agents such as phosphates may be employed.

The following example is not limiting but is illustrative of the process of this invention.

EXAMPLE

| Ingredients | Amounts Grams | CC |
| --- | --- | --- |
| Part I | | |
| Polyvinylpyrrolidone | 90.00 | |
| Purified Water q.s. ad | | 10,000 |
| Part II | | |
| Sodium Chloride | 382.00 | |
| Disodium Edetate, recrystallized | 4.50 | |
| Boric Acid, N.F. | 45.00 | |
| Chlorhexidine Gluconate (20% solution) | | 11.25 |
| Thimerosal, N.F. | 1.03 | |
| Purified Water, q.s. ad | | 30,000 |

Part I. 10 liters of purified water is heated in a 30 liter container to about 85° C. and the polyvinylpyrrolidone added with vigorous mixing. The mixing is continued for about one hour. The container is sealed with paper and foil and autoclaved for about 90 minutes at 121° C. plus 15 PSI pressure. The solution is then allowed to cool to room temperature.

Part II. A portion of the 30 liters of purified water (approximately 20 liters) is measured and the ingredients added in the order shown while mixing. Each ingredient is allowed to dissolve or be well mixed before adding the next. Adjust pH to 7.40 with 1 normal sodium hydroxide and bring volume to 30 liters with distilled water and stir to mix.

Part II is then sterile filtered into Part I through a 0.2 micron Gelman Acroflow 121 5" filter. The volume is brought to 30 liters with sterile filtrate.

The fraction containing the PVP and which was heated separately, Part I, must be cooled before adding the Part II which contains thimerosal. It was discovered that heat degraded the thimerosal. For example, if all the ingredients are mixed and heated together there is an initial loss of thimerosal followed by slow degradation. Unacceptable changes in other solution components also occur.

What is claimed is:

1. A process for manufacturing a solution containing the combination of polyvinylpyrrolidone and thimerosal which comprises heating an aqueous solution of polyvinylpyrrolidone to a temperature of about 85° C. to about 121° C., cooling said polyvinylpyrrolidone solution and adding an antibacterial or antifungal amount of thimerosal to said cooled polyvinylpyrrolidone.

2. The process of claim 1 in which the polyvinylpyrrolidone solution is heated from about 85° C. to about 121° C. for about 30 to about 180 minutes.

3. The process of claim 2 in which the pressure is from atmospheric to atmospheric plus 15 PSI.

4. The process of claim 1 in which the final concentration of polyvinylpyrrolidone in the solution is from about 0.01% to about 1.0% W/V.

5. The process of claim 1 in which said solution is used as a contact lens care preparation.

6. The process of claim 1 in which said solution is used as an ophthalmic preparation.

* * * * *